(12) United States Patent
Bokel et al.

(10) Patent No.: US 7,045,629 B2
(45) Date of Patent: May 16, 2006

(54) METHOD FOR PRODUCING-2[-5-(4-FLUOROPHENYL)-3-PYRIDYLMETHYLAMINOMETHYL]-CHROMANE

(75) Inventors: Heinz-Hermann Bokel, Darmstadt (DE); Steffen Neuenfeld, Messel (DE); Ludwig Gantzert, Pfungstadt (DE); Ralf Knierieme, Gross-Zimmern (DE); Elke Simon, Gross-Zimmern (DE); Ralf Devant, Darmstadt (DE); Udo Helm, Michelstadt (DE); Helmut Reubold, Bad Koenig (DE)

(73) Assignee: Merck Patent GmbH, Darmstadt (DE)

( * ) Notice: Subject to any disclaimer, the term of this patent is extended or adjusted under 35 U.S.C. 154(b) by 28 days.

(21) Appl. No.: 10/475,988

(22) PCT Filed: Apr. 8, 2002

(86) PCT No.: PCT/EP02/03857

§ 371 (c)(1),
(2), (4) Date: Oct. 27, 2003

(87) PCT Pub. No.: WO02/088117

PCT Pub. Date: Nov. 7, 2002

(65) Prior Publication Data

US 2004/0138266 A1    Jul. 15, 2004

(30) Foreign Application Priority Data

Apr. 26, 2001  (DE) .............................. 101 20 619

(51) Int. Cl.
*C07D 401/00*    (2006.01)
(52) U.S. Cl. ...................................... 546/207; 548/542

(58) Field of Classification Search ................ 546/207; 548/542
See application file for complete search history.

(56) References Cited

U.S. PATENT DOCUMENTS

| 5,318,988 A | 6/1994 | Schohe-Loop et al. |
| 5,767,132 A | 6/1998 | Boettcher et al. |

FOREIGN PATENT DOCUMENTS

| DE | 10005150 A | 8/2001 |
| FR | 2701479 A | 8/1994 |
| WO | WO 9418193 A1 | 8/1994 |
| WO | WO 0158873 A1 | 8/2001 |

OTHER PUBLICATIONS

Baraldi et al, "Resolution of A CPzl Precursor, synthesis and Biological Evaluation of (+) and (-) -N-Boc-CPzl", Bioorganic and Medicinal Chemistry letters 9 (1999) 3087-3092.*

* cited by examiner

*Primary Examiner*—Rita Desai
*Assistant Examiner*—Raymond Covington
(74) *Attorney, Agent, or Firm*—Millen, White, Zelano & Branigan, P.C.

(57) ABSTRACT

The present invention relates to a process for the preparation of 2-[5-(4-fluorophenyl)-3-pyridylmethylaminomethyl] chroman, the enantiomers and its salts, characterised in that 5-(4-fluorophenyl)pyridine-3-carbaldehyde is reacted directly with aminomethylchroman or its salts under reducing conditions to give 2-[5-(4-fluorophenyl)-3-pyridylmethylaminomethyl]chroman, and the latter is, if desired, converted into one of its physiologically acceptable salts by treatment with an acid.

15 Claims, 2 Drawing Sheets

METHOD FOR PRODUCING-2[-5-(4-FLUOROPHENYL)-3-PYRIDYLMETHYLAMINOMETHYL]-CHROMANE

Figure 1:
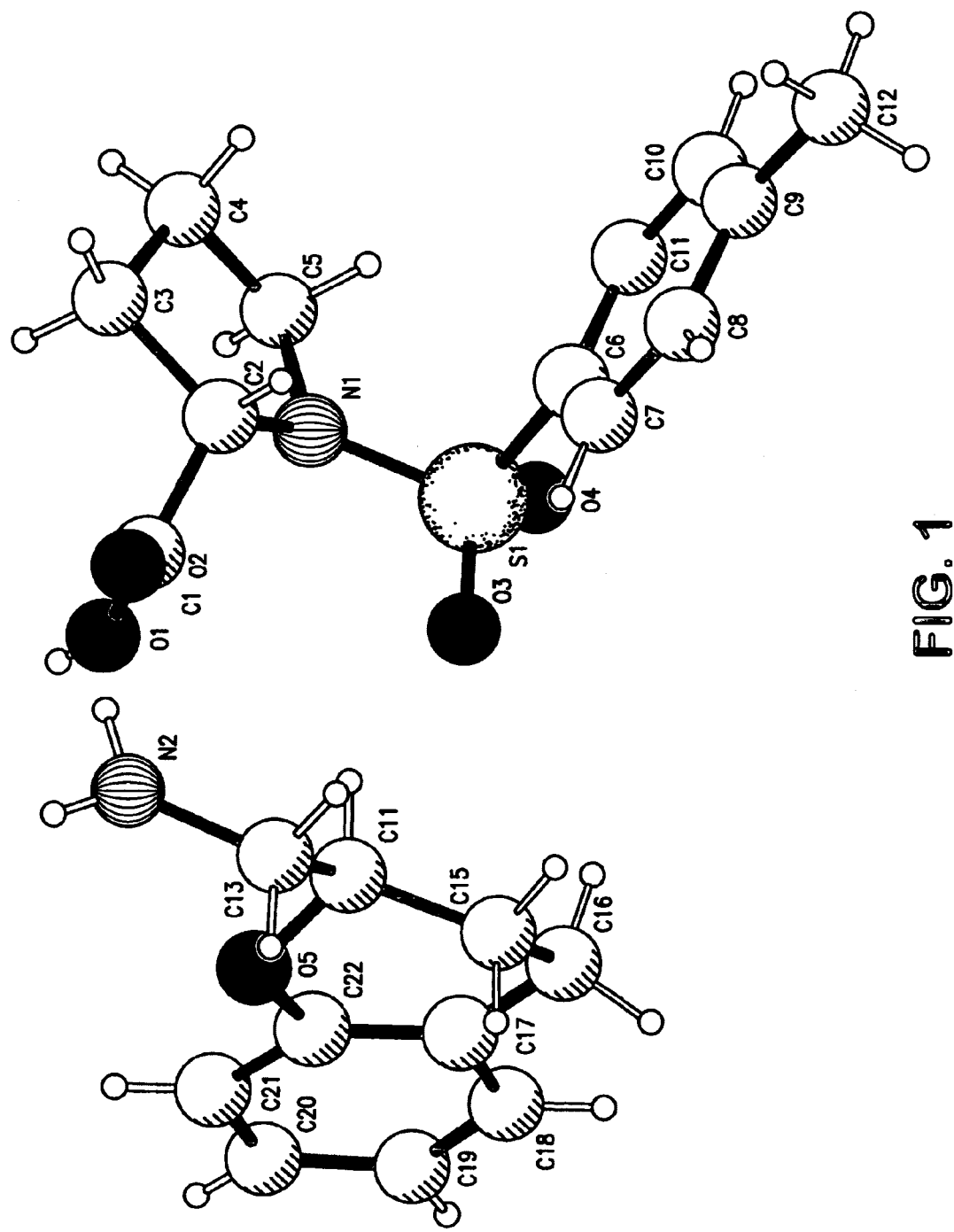

The invention relates to a process for the preparation of 2-[5-(4-fluorophenyl)-3-pyridylmethylaminomethyl]chroman of the formula I

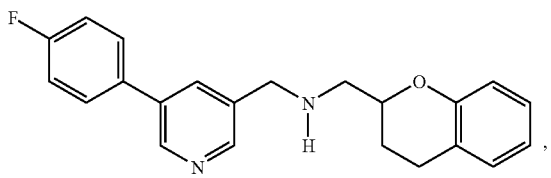

including the enantiomerically pure compounds of the formula I, and its salts, characterised in that 5-(4-fluorophenyl)pyridine-3-carbaldehyde is reacted directly with 2-aminomethylchroman or its salts under reducing conditions to give the compound of the formula I, and the resulting compound of the formula I is, if desired, converted into one of its salts by treatment with an acid.

The compound 2-[5-(4-fluorophenyl)-3-pyridylmethylaminomethyl]chroman is disclosed in U.S. Pat. No. 5,767,132 both as the racemate and as enantiomerically pure compounds. U.S. Pat. No. 5,767,132 likewise describes the preparation of the physiologically acceptable salts (column 9, lines 6 to 32) and a preparation process (Examples 5 and 19).

2-[5-(4-Fluorophenyl)-3-pyridylmethylaminomethyl]chroman of the formula I and its salts are selective dopamine $D_2$ receptor antagonists and 5-$HT_{1A}$ receptor agonists. They are therefore suitable for use for the preparation of a medicament for the prophylaxis and/or treatment of secondary illnesses after cerebral infarction (apoplexia cerebri), for example strokes and cerebral ischaemia, for the prophylaxis and control of cerebral disorders, for example migraine, treatment of anxiety, tension and depression states, sexual dysfunctions with central nervous causes, sleep and nutrient uptake disorders or for the treatment of psychoses, for example schizophrenia, schizoaffective psychoses or cyclothymia.

The term "anxiety states" is also taken to mean the syndromes of panic disorder with and without agoraphobia, compulsive disorders or obsessive personality disorder, specific anxiety disorder, social anxiety disorder, acute stress disorder, post-traumatic stress disorder, generalised anxiety disorder, substance-induced anxiety disorder and also an anxiety disorder due to a medical illness factor.

2-[5-(4-Fluorophenyl)-3-pyridylmethylaminomethyl]chroman of the formula I and its salts are furthermore suitable for the elimination of cognitive deficits, for the improvement of learning and memory ability and for the treatment of Alzheimer's disease. They can likewise be employed for the treatment of side-effects in hypertonia treatment, in endocrinology and gynaecology, for example for the treatment of acromegalia, hypogonadism, secondary amenorrhoea, premenstrual syndrome or undesired puerperal lactation.

The compounds can therefore be used as medicament active ingredients in human and veterinary medicine. They can furthermore be used as intermediates for the preparation of further medicament active ingredients.

Since 2-[5-(4-fluorophenyl)-3-pyridylmethylaminomethyl]chroman, in particular (R)-(−)-2-[5-(4-fluorophenyl)-3-pyridylmethylaminomethyl]chroman, but also (S)-(+)-2-[5-(4-fluorophenyl)-3-pyridylmethylaminomethyl]chroman, and its salts are very promising as medicament active ingredients, the preparation is of very considerable interest.

The object of the present invention was therefore to find a novel and effecttive synthesis variant for the compounds described above.

In the previously known synthesis of 2-[5-(4-fluorophenyl)-3-pyridylmethylaminomethyl]chroman as the racemate and as enantiomerically pure compounds, described in U.S. Pat. No. 5,767,132, Examples 5 and 19, 2-aminomethylchroman, both as the racemate and as enantiomerically pure compounds, or a corresponding salt of these compounds, is reacted with 3-(chloromethyl)-5-(4-fluorophenyl)pyridine. However, the starting material 3-(chloromethyl)-5-(4-fluorophenyl)pyridine is a skin irritant and may cause allergies. Furthermore, "haloamino compounds", such as, for example, 3-(chloromethyl)-5-(4-fluorophenyl)pyridine, have a tendency towards exothermic decomposition since alkylating and alkylatable functional groups are present simultaneously in a single molecule (lit.: Chem.-Ing.-Tech. 1979, 51, 928–933).

The invention therefore relates to a process for the preparation of 2-[5-(4-fluorophenyl)-3-pyridylmethylaminomethyl]chroman of the formula I

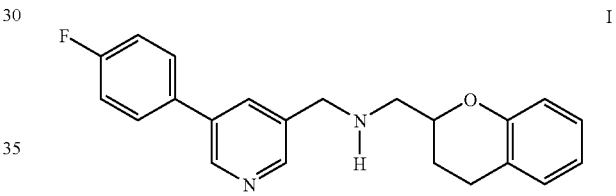

and its salts, characterised in that
(1) 5-(4-fluorophenyl)pyridine-3-carbaldehyde of the formula II

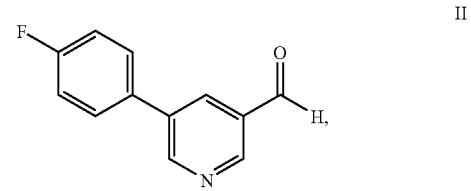

is reacted directly with 2-aminomethylchroman or its salts under reducing conditions to give the compound of the formula I, and
(2) the resultant compound of the formula I is converted into one of its salts by treatment with an acid.

The advantage of the novel process over the process disclosed in U.S. Pat. No. 5,767,132 consists in the reduction of by-product by suppression of double alkylation. After conversion to the process, the active ingredient contains no by-product having two arylpyridine radicals, which simplifies purification of the active ingredient.

Compared with the preparation variants of secondary amines disclosed in the standard literature by reaction of aldehydes with primary amines (lit.: Houben-Weyl, Methoden der organischen Chemie [Methods of Organic Chemistry], Volume 11/1), it is not necessary in the process according to the invention to force the elimination of water to give the aldimine as intermediate. Instead, the aldehyde, in accordance with the invention 5-(4-fluorophenyl)pyridine-3-carbaldehyde, can be combined directly with 2-aminomethylchroman under reducing conditions.

The advantage over the reductive aminations taking place under standard conditions consequently consists in that a smaller number of reagents and a lower thermal load are necessary. This likewise results in fewer impurities and side reactions. In particular, heating for a number of hours in an azeotrope-forming solvent with addition of a catalyst, i.e. an acid, for example p-toluenesulfonic acid, is unnecessary. Typical side reactions of thermally loaded aldehydes are, for example, disproportionation to the alcohol and acid or oligomerisation with elimination of water, for example to give the substituted trioxane.

In addition, it has been found that the reactive form of 2-aminomethylchroman (free base) does not have to be prepared separately, but instead can be prepared in situ directly from a storage-stable salt form of the amine. The omission of isolation of the free base means that at least one liquid/liquid partition is unnecessary. This additionally restricts the consumption of solvent.

The invention therefore relates to a process, as described above, characterised in that the reactive form of 2-aminomethylchroman is prepared in situ from a salt of 2-aminomethylchroman.

Particularly suitable salts of 2-aminomethylchroman are 2-aminomethylchroman maleate, 2-aminomethylchroman hydrochloride and 2-aminomethylchroman carbonate. Particularly advantageous in accordance with the invention is the use of 2-aminomethylchroman hydrochloride.

2-[5-(4-Fluorophenyl)-3-pyridylmethylaminomethyl] chroman of the formula I contains a chiral centre in the 2-position of the chroman structure and can therefore exist in racemic or optically active form. The formula I covers both the racemate and the enantiomerically pure compounds (R)-(−)-2-[5-(4-fluorophenyl)-3-pyridylmethylaminomethyl]chroman and (S)-(+)-2-[5-(4-fluorophenyl)-3-pyridylmethylaminomethyl]chroman.

Racemates, including the racemate of 2-[5-(4-fluorophenyl)-3-pyridylmethylaminomethyl]chroman, can be resolved mechanically or chemically into the isomers by methods known per se. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid or amino acids, or the various optically active camphorsulfonic acids, such as β-camphorsulfonic acid.

Also advantageous is chromatographic enantiomer separation with the aid of a column packed with an optically active resolving agent (for example dinitrobenzoylphenylglycine); an example of a suitable eluent is a hexane/isopropanol/acetonitrile mixture, for example in the volume ratio 82:15:3, or as described, for example, in WO 97147617.

Diastereomer resolution can also be carried out by standard purification processes, such as, for example, fractional crystallisation (lit.: A. Collet, S. H. Wilen, Enantiomers, Racemates and Resolutions, Wiley (New York) 1981).

It is of course also possible to obtain optically active compounds of the formula I by the above-described processes by using 2-aminomethylchroman which is already optically active [(R)-2-aminomethylchroman or (S)-2-aminomethylchroman].

Racemic 2-aminomethylchroman is commercially available or can be prepared by known synthetic methods.

(R)- or (S)-2-Aminomethylchroman can be prepared by known synthetic methods.

The preparation can be carried out, for example, starting from commercially available chroman-2-carboxylic acid by the following reactions:
(1) reaction with thionyl chloride to give the carboxylic acid chloride,
(2) reaction with a chiral amine to give a diastereomer mixture of the carboxamide,
(3) diastereomer resolution by conventional methods as described above,
(4) reduction of the diastereomeric carboxamide to the corresponding N-substituted 2-aminomethylchroman, and
(5) dealkylation, for example by catalytic hydrogenation, to give enantiomerically pure 2-aminomethylchroman. Either the (R) or the (S) enantiomer is obtained, depending on the configuration of the chiral amine.

The invention likewise relates to a process for the preparation of (R)-(−)-2-[5-(4-fluorophenyl)-3-pyridylmethylaminomethyl]chroman of the formula Ia

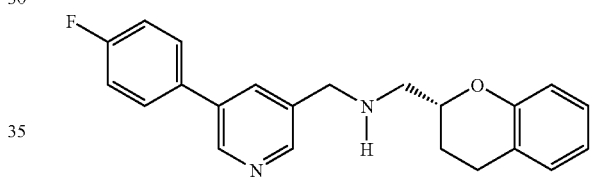

Ia and its salts, characterised in that
(1) 5-(4-fluorophenyl)pyridine-3-carbaldehyde of the formula II

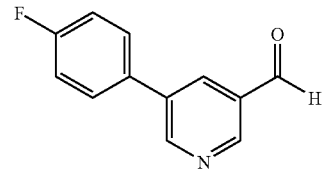

II is reacted directly with (R)-2-aminomethylchroman or its salts under reducing conditions to give the compound of the formula Ia, and
(2) the resultant compound of the formula Ia is converted into one of its salts by treatment with an acid. The (S) enantiomer of the compound I is obtained in an analogous manner using (S)-2-aminomethylchroman.

Alternatively, (R)-2-aminomethylchroman can also be prepared by reaction of racemic 2-aminomethylchroman with (S)-N-tosylproline followed by racemate resolution by crystallisation. The solubilities of the two diastereomeric salts of the racemic amine with enantiomerically pure N-tosyl-(S)-proline are so different that the pure (R)/(S) diastereomer of the formula III can be obtained by normal crystallisation. Consequently, (R)-2-aminomethylchroman N-(toluenesulfonyl)-(S)-prolinate of the formula III

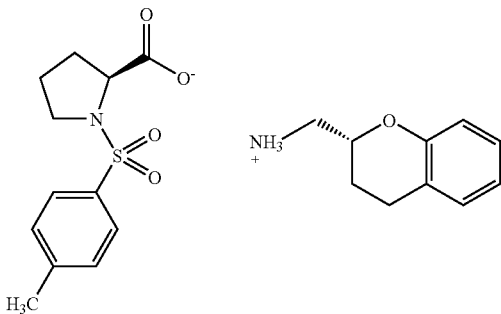

is formed.

Enantiomerically pure (R)-2-aminomethylchroman is subsequently liberated from the compound of the formula III by basic extraction. (S)-2-aminomethylchroman is obtained in an analogous manner using (R)-N-tosylproline.

The invention furthermore relates to a process for the preparation of (S)-(+)-2-[5-(4-fluorophenyl)-3-pyridylmethylaminomethyl]chroman or salts thereof, characterised in that (S)-aminomethylchroman, prepared from racemic aminomethylchroman racemate resolution using (S)-N-tosylproline, is employed.

The invention likewise relates to the diastereomeric salt (S)-2-aminomethylchroman N-(toluenesulfonyl)-(R)-prolinate.

The compound of the formula III is a valuable intermediate in the synthesis of (R)-(−)-2-[5-(4-fluorophenyl)-3-pyridylmethylaminomethyl]chroman and its salts, as described above.

The invention therefore relates to a process for the preparation of (R)-(−)-2-[5-(4-fluorophenyl)-3-pyridylmethylaminomethyl]chroman or its salts, as described above, characterised in that (R)-aminomethylchroman, prepared from racemic aminomethylchroman by racemate resolution using (S)-N-tosylproline, is employed.

The invention likewise relates to the diastereomeric salt (R)-2-aminomethylchroman N-(toluenesulfonyl)-(S)-prolinate.

Figure 2:
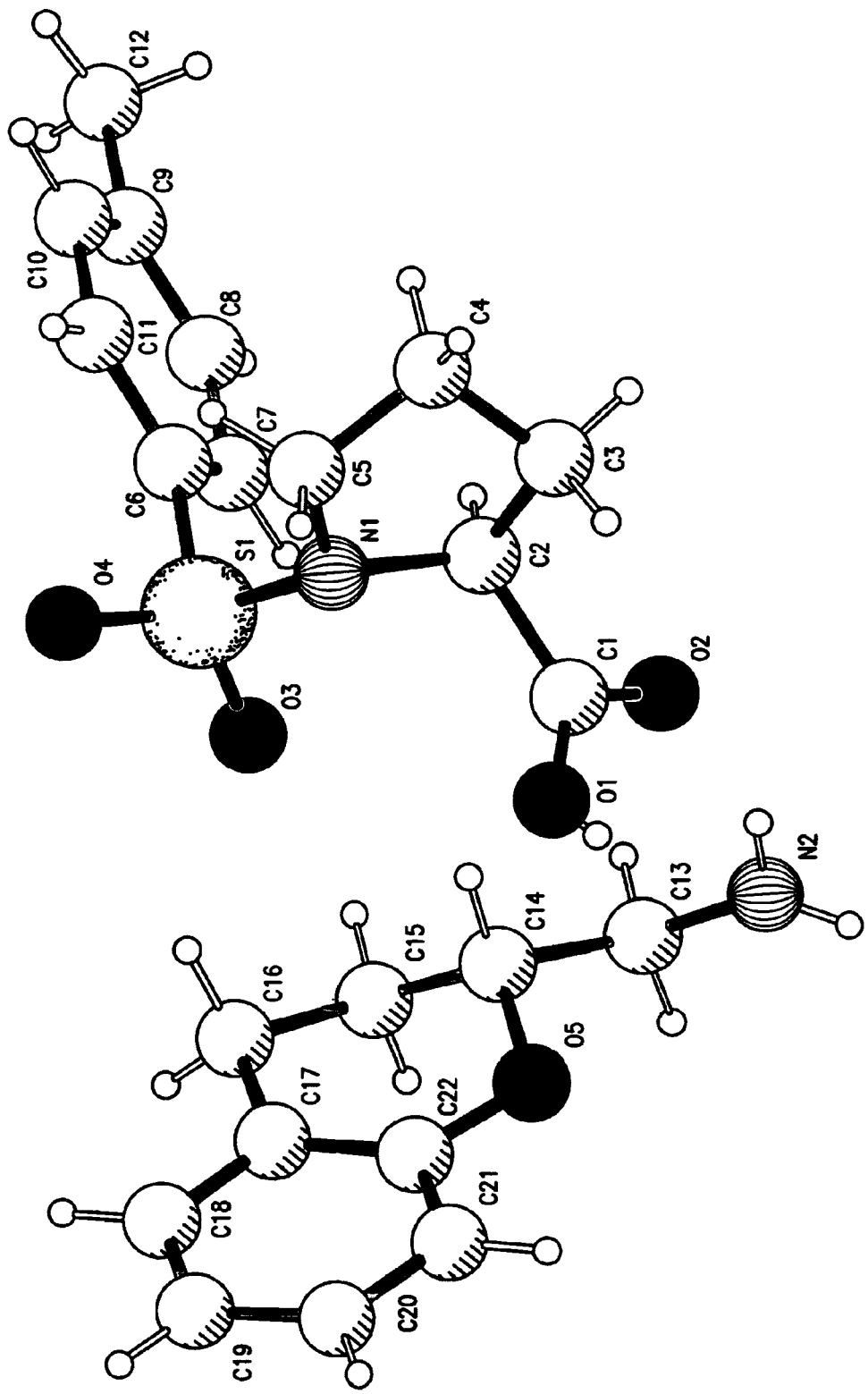

The preparation of (R)-2-aminomethylchroman N-(toluenesulfonyl)-(S)-prolinate and the subsequent basic extraction are described in Example 4. The X-ray structural analysis of the salt is shown in FIG. 1 and FIG. 2. The relative configuration of the two centres of asymmetry can be confirmed by FIGS. 1 and 2. The configuration of (R)-2-aminomethylchroman can be derived from the absolute configuration of the natural amino acid (S)-proline.

FIG. 1: X-ray structural analysis of (R)-2-aminomethylchroman N-(toluenesulfonyl)-(S)-prolinate;

FIG. 2: X-ray structural analysis of (S)-2-aminomethylchroman N-(toluenesulfonyl)-(S)-prolinate.

5-(4-Fluorophenyl)pyridine-3-carbaldehyde can be prepared by known synthetic methods. The preparation can be carried out, for example, starting from commercially available 5-(4-fluorophenyl)nicotinic acid by the following reactions:

(1) reduction to 5-(4-fluorophenyl)-3-hydroxymethylpyridine, for example in the presence of borohydrides, and subsequent (2) oxidation of the alcohol, for example using manganese dioxide ($MnO_2$), to give the desired aldehyde.

A further alternative is preparation of the aldehyde by reduction of 3-cyano-5-(4-fluorophenyl)pyridine, for example by hydrogenation or using hydrides, such as diisobutylaluminium hydride or lithium tri-tert-butoxyaluminium hydride.

The reaction of 5-(4-fluorophenyl)pyridine-3-carbaldehyde with 2-aminomethylchroman hydrochloride, in particular (R)-2-aminomethylchroman hydrochloride, is carried out under reducing reaction conditions, for example in the presence of borohydrides or hydrogenation catalysts.

Suitable borohydrides are lithium borohydride, sodium borohydride, sodium cyanoborohydride, potassium borohydride or boron hydride on polymeric support materials, for example Amberlyst A-26 $BH_4^-$ form. Particular preference is given to sodium borohydride which has first been reacted with methanol to give sodium trimethoxyborohydride.

Any solvent is suitable for the reaction in the presence of borohydrides so long as it does not interfere with the starting materials. Particularly suitable are protic solvents, for example alcohols, such as ethanol or methanol, or mixtures thereof.

Suitable reaction temperatures are between 0° and 70°, preferably between 10 and 50°, particularly preferably between 20 and 35° C.

The invention also relates to a process as described above, characterised in that the reaction is carried out in the presence of a borohydride.

The reaction of 5-(4-fluorophenyl)pyridine-3-carbaldehyde with 2-aminomethylchroman hydrochloride, in particular (R)-2-aminomethylchroman hydrochloride, can likewise be carried out in the presence of hydrogen gas and hydrogenation catalysts.

Suitable hydrogenation catalysts are, for example, metals from the eighth sub-group, for example Raney nickel, palladium or platinum. Palladium or platinum catalysts may be present on a support material, for example on activated carbon, calcium carbonate, barium sulfate or strontium carbonate, in the form of their oxides, for example platinum oxide, or in finely divided form.

The reaction is preferably carried out at a pressure of from 1 to 200 bar and at temperatures between −80° and +150° C., particularly preferably at room temperature and atmospheric pressure.

Suitable solvents are, for example, alcohols, such as methanol, ethanol or isopropanol, carboxylic acids, such as acetic acid, esters, such as ethyl acetate, or ethers, such as tetrahydrofuran (THF) or dioxane. It is likewise possible to employ solvent mixtures of the above-mentioned solvents, if desired also solvent mixtures containing water.

The invention therefore relates to a process as described above, characterised in that the reaction is carried out in the presence of hydrogen and a hydrogenation catalyst.

The base of the formula I obtained can be converted into the associated acid-addition salt using an acid. Suitable acids for this reaction are those which give physiologically acceptable salts. Thus, it is possible to use inorganic acids, for example sulfuric acid, hydrohalic acids, such as hydrochloric acid or hydrobromic acid, phosphoric acids, such as orthophosphoric acid, nitric acid, sulfamic acid, furthermore organic acids, specifically aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumareic acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids and laurylsulfuric acid.

In a preferred embodiment, the salt formation is carried out in ethanol by precipitation with hydrochloric acid (37%), giving 2-[5-(4-fluorophenyl)-3-pyridylmethylaminomethyl] chroman dihydrochloride hemihydrate, (R)-(−)-2-[5-(4-fluorophenyl)-3-pyridylmethylaminomethyl]chroman dihydrochloride hemihydrate or (S)-(+)-2-[5-(4-fluorophenyl)-3-pyridylmethylaminomethyl]-chroman dihydrochloride hemihydrate.

The invention relates to a process as described above, characterised in that (R)-(−)-2-[5-(4-fluorophenyl)-3-pyridylmethylaminomethyl]chroman dihydrochloride or (S)-(+)-2-[5-(4-fluorophenyl)-3-pyridylmethylaminomethyl] chroman dihydrochloride is prepared.

In a likewise preferred embodiment, the salt formation is carried out at −5° C. by addition of the stoichiometric amount of 37% aqueous hydrochloric acid to a 7% solution of the base in ethanol, giving (R)-(−)-2-[5-(4-fluorophenyl)-3-pyridylmethylaminomethyl]chroman hydrochloride or (S)-(+)-2-[5-(4-fluorophenyl)-3-pyridylmethylaminomethyl]chroman hydrochloride.

The invention relates in particular to the process as described above, characterised in that (R)-(−)-2-[5-(4-fluorophenyl)-3-pyridylmethylaminomethyl]chroman hydrochloride is prepared.

Even without further comments, it is assumed that a person skilled in the art will be able to utilise the above description in the broadest scope. The preferred embodiments should therefore merely be regarded as descriptive disclosure which is absolutely not limiting in any way.

All temperature details above and below are given in ° C. In the following examples, "conventional work-up" means that water is added if necessary, the pH is, if necessary, adjusted to between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation.

EXAMPLE 1

20.3 g of (R)-2-aminomethylchroman hydrochloride are introduced into 150 ml of ethanol, and 36.8 g of a 20% solution of sodium ethoxide in ethanol are added dropwise with stirring. 20.5 g of 5-(4-fluorophenyl)pyridine-3-carbaldehyde are added to the suspension at 35° C., and the mixture is stirred for a further 3 hours. After addition of 4.2 g of sodium borohydride, the mixture is stirred for a further 4 hours, and 62 ml of water are then added dropwise at room temperature. The pH of the reaction mixture is then adjusted to pH 4 using 37% hydrochloric acid over the course of one hour. The crystals are filtered off, rinsed with ethanol and dried under reduced pressure, giving 27.2 g of (R)-(−)-2-[5-(4-fluorophenyl)-3-pyridylmethylaminomethyl]chroman hydrochloride (69% yield).

EXAMPLE 2

20.27 g of 2-aminomethylchroman hydrochloride are introduced into 130 g of methanol, and 20.4 g of a 30% sodium methoxide solution in methanol are subsequently added. 20.43 g of 5-(4-fluorophenyl)pyridine-3-carbaldehyde are added to the white suspension at 35° C., and the mixture is stirred for 1.5 hours before 4.20 g of sodium borohydride are added in portions. After 15 hours, 56.4 ml of water are added, and the pH of the mixture is adjusted to pH 2 using 37% hydrochloric acid. After the suspension has been cooled to 0° C., the crystals are filtered off, washed with methanol and dried under reduced pressure, giving 28.2 g of 2-[5-(4-fluorophenyl)-3-pyridylmethylaminomethyl] chroman hydrochloride (64% yield).

EXAMPLE 3

5.07 g of (R)-2-aminomethylchroman and 5.00 g of 5-(4-fluorophenyl)-pyridine-3-carbaldehyde are dissolved in 38 ml of THF, and 6 g of 5% palladium on activated carbon are added with stirring. The mixture is hydrogenated at room temperature under atmospheric pressure with stirring. When the take-up of hydrogen is complete, the catalyst is filtered off, giving 8.66 g of (R)-(−)-2-[5-(4-fluorophenyl)-3-pyridylmethylaminomethyl]chroman by removal of the solvent by distillation (68% yield).

EXAMPLE 4

(1) 45.0 g of (S)-proline are added to a solution of 31.0 g of NaOH in 300 ml of water. When the solid has dissolved, 74.6 g of p-toluenesulfonyl chloride are added, and the mixture is stirred at 70° C. for 4 hours. After the mixture has been cooled to room temperature, 30 ml of 37% hydrochloric acid are added, and the solution is extracted a number of times with methyl tert-butyl ether. The collected organic phases are evaporated, and the residue is dissolved in 60 ml of ethanol. This mixture is subsequently slowly added dropwise to a solution of 42.2 g of rac-2-aminomethylchroman in 200 ml of ethanol. The resultant precipitate is filtered off, washed with ethanol and dried, giving 43.0 g of (R)-2-aminomethylchroman N-(toluenesulfonyl)-(S)-prolinate (77% of theory), characterised by FIGS. 1 and 2.

(2) 20.4 g of (R)-2-aminomethylchroman N-(toluenesulfonyl)-(S)-prolinate are suspended in 60 ml of toluene and extracted with a solution of 2.07 g of NaOH in 40 ml of water. The aqueous phase is re-extracted with toluene and evaporated together with the first organic phase. The residue is dissolved in 500 ml of ethanol, and 4.88 g of 37% hydrochloric acid are then added. After the mixture has been stirred at room temperature, the suspension is cooled to −10° C., and the crystalline solid is filtered off, giving 7.95 g of (R)-(−)-2-[5-(4-fluorophenyl)-3-pyridylmethylaminomethyl]chroman hydrochloride after drying to constant weight (85% of theory).

The substance is enantiomerically pure according to HPLC.

HPLC data:

Column: Daicel Crownpak CR(+) (150*4 mm, packing material 5 μm)

Mobile phase: 90% water (adjusted to pH 2.0 using HClO$_4$), 10% methanol

Flow rate: 1.2 ml/minute

Retention time: 53 minutes.

What is claimed is:

1. A process for preparing 2-[5-(4-fluorophenyl)-3-pyridylmethylaminomethyl]chroman of formula I

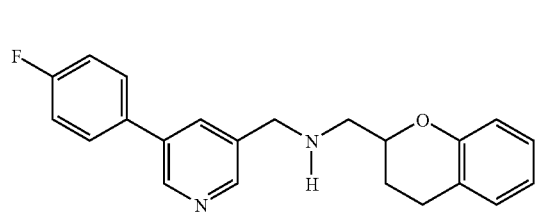

or a salt thereof, comprising
(1) reacting 5-(4-fluorophenyl)pyridine-3-carbaldehyde of formula II

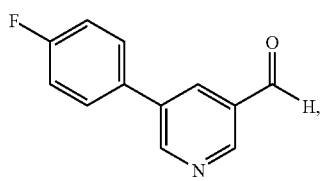

directly with 2-aminomethylchroman or a salt thereof under reducing condition to give the compound of formula I, and optionally
(2) converting the compound of the formula I prepared in (1) into one of its salts by treatment with an acid.

2. A process according to claim 1, wherein the 2-aminomethylchroman is prepared in situ from a salt of aminomethylchroman.

3. A process according to claim 1, wherein the reaction is carried out in the presence of a borohydride.

4. A process according to claim 1, wherein the reaction is carried out in the presence of hydrogen and a hydrogenation catalyst.

5. A process according to claim 1, wherein (R)-(−)-2-[5-(4-fluorophenyl)-3-pyridylmethylaminomethyl]chroman or a salt thereof is prepared.

6. A process according to claim 1, wherein the 2-aminomethylchroman is (R)-aminomethylchroman prepared from racemic aminomethylchroman by racemate resolution using (S)-N-tosylproline.

7. A process according to claim 1, wherein (R)-(−)-2-[5-4-fluorophenyl)-3-pyridylmethylaminomethyl]chroman hydrochloride is prepared.

8. A process according to claim 1, wherein (R)-(−)-2-[5-(4-fluorophenyl)-3-pyridylmethylaminomethyl]chroman dihydrochloride is prepared.

9. A process for preparing 2-[5-(4-fluorophenyl)-3-pyridylmethylaminomethyl]chroman of formula I

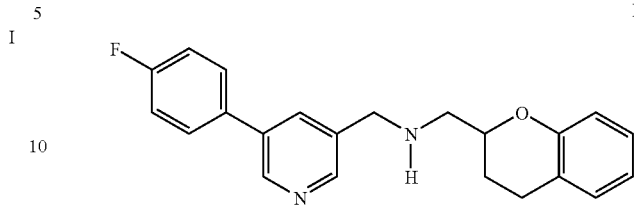

or a salt thereof, comprising
(1) reacting 5-(4-fluorophenyl)pyridine-3-carbaldehyde of formula II

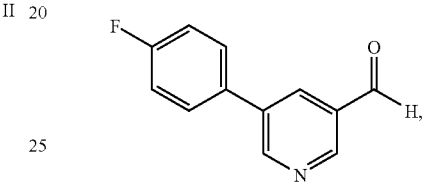

directly with 2-aminomethylchroman or a salt thereof under reducing condition without the presence of a catalyst to give the compound of formula I, and optionally
(2) converting the compound of the formula I prepared in (1) into one of its salts by treatment with an acid.

10. A process according to claim 9, wherein the 2-aminomethylchroman is prepared in situ from a salt of aminomethylchroman.

11. A process according to claim 9, wherein the reaction is carried out in the presence of a borohydride.

12. A process according to claim 9, wherein (R)-(−)-2-[5-(4-fluorophenyl)-3-pyridylmethylaminomethyl]chroman or a salt thereof is prepared.

13. A process according to claim 9, wherein the 2-aminomethylchroman is (R)-aminomethylchroman prepared from racemic aminomethylchroman by racemate resolution using (S)-N-tosylproline.

14. A process according to claim 9, wherein (R)-(−)2-[5-(4-fluorophenyl)-3-pyridylmethylaminomethyl]chroman hydrochloride is prepared.

15. A process according to claim 9, wherein (R)-(−)-2-[5-(4-fluorophenyl)-3-pyridylmethylaminomethyl]chroman dihydrochloride is prepared.

* * * * *